(12) United States Patent
Alamin et al.

(10) Patent No.: US 9,295,499 B2
(45) Date of Patent: Mar. 29, 2016

(54) METHODS AND SYSTEMS FOR LATERALLY STABILIZED CONSTRAINT OF SPINOUS PROCESSES

(71) Applicants: Todd Alamin, Woodside, CA (US); Ian Bennett, San Francisco, CA (US); Colin Cahill, Portola Valley, CA (US); Louis Fielding, San Carlos, CA (US); Manish Kothari, San Rafael, CA (US); Jeffrey Schwardt, Palo Alto, CA (US)

(72) Inventors: Todd Alamin, Woodside, CA (US); Ian Bennett, San Francisco, CA (US); Colin Cahill, Portola Valley, CA (US); Louis Fielding, San Carlos, CA (US); Manish Kothari, San Rafael, CA (US); Jeffrey Schwardt, Palo Alto, CA (US)

(73) Assignee: Empirical Spine, Inc., Woodside, CA (US)

( * ) Notice: Subject to any disclaimer, the term of this patent is extended or adjusted under 35 U.S.C. 154(b) by 136 days.

(21) Appl. No.: 13/889,581

(22) Filed: May 8, 2013

(65) Prior Publication Data

US 2013/0253584 A1    Sep. 26, 2013

Related U.S. Application Data

(60) Continuation of application No. 13/206,339, filed on Aug. 9, 2011, now Pat. No. 8,454,660, which is a division of application No. 11/777,366, filed on Jul. 13, 2007, now Pat. No. 8,029,541, application No.

(Continued)

(51) Int. Cl.
*A61B 17/70* (2006.01)
*A61B 17/84* (2006.01)

(52) U.S. Cl.
CPC .......... *A61B 17/7062* (2013.01); *A61B 17/7055* (2013.01); *A61B 17/842* (2013.01)

(58) Field of Classification Search
CPC ............. A61B 17/562; A61B 17/6425; A61B 17/7004; A61B 17/7013; A61B 17/7014; A61B 17/7019; A61B 17/702; A61B 17/7022; A61B 17/7023; A61B 17/7025; A61B 17/7026; A61B 17/7028; A61B 17/7029; A61B 17/7031; A61B 17/7047; A61B 17/7062; A61B 17/7064; A61B 17/7067; A61B 17/7068; A61B 17/707; A61B 17/7071; A61B 17/82; A61B 17/7053
See application file for complete search history.

(56) References Cited

U.S. PATENT DOCUMENTS

| 3,648,691 A | 3/1972 | Lumb et al. |
| 4,246,660 A | 1/1981 | Wevers |

(Continued)

FOREIGN PATENT DOCUMENTS

| EP | 0322334 A1 | 6/1989 |
| EP | 0743045 A2 | 11/1996 |

(Continued)

OTHER PUBLICATIONS

U.S. Appl. No. 13/958,323, filed Aug. 2, 2013, Alamin et al.

(Continued)

*Primary Examiner* — Pedro Philogene
*Assistant Examiner* — Lynnsy Summitt
(74) *Attorney, Agent, or Firm* — Wilson Sonsini Goodrich & Rosati (57) ABSTRACT

A spinal implant for limiting flexion of the spine includes a tether structure for encircling adjacent spinal processes. Usually, a pair of compliance members will be provided as part of the tether structure for elastically limiting flexion while permitting an extension. A cross-member is provided between the compliance member or other portions of the tether structure to stabilize the tether structure and prevent misalignment after implantation.

14 Claims, 7 Drawing Sheets

Related U.S. Application Data

13/889,581, which is a continuation-in-part of application No. 13/455,917, filed on Apr. 25, 2012, now abandoned, which is a division of application No. 12/426,167, filed on Apr. 17, 2009, now Pat. No. 8,187,307, which is a continuation-in-part of application No. PCT/US2007/081815, filed on Oct. 18, 2007, application No. 13/889,581, which is a continuation-in-part of application No. 13/427,551, filed on Mar. 22, 2012, now Pat. No. 8,790,372, which is a division of application No. 12/426,119, filed on Apr. 17, 2009, now Pat. No. 8,162,982, which is a continuation-in-part of application No. PCT/US2007/081822, filed on Oct. 18, 2007, application No. 13/889,581, which is a continuation-in-part of application No. 13/274,171, filed on Oct. 14, 2011, now abandoned, which is a continuation of application No. PCT/US2010/031471, filed on Apr. 16, 2010, application No. 13/889,581, which is a continuation-in-part of application No. 12/106,049, filed on Apr. 18, 2008, now abandoned, which is a continuation-in-part of application No. 11/875,674, filed on Oct. 19, 2007, now abandoned, said application No. PCT/US2010/031471 is a continuation of application No. 12/426,119.

(60) Provisional application No. 60/862,085, filed on Oct. 19, 2006, provisional application No. 61/158,892, filed on Mar. 10, 2009.

(56) References Cited

U.S. PATENT DOCUMENTS

| | | | |
|---|---|---|---|
| 4,643,178 | A | 2/1987 | Nastari et al. |
| 4,708,132 | A | 11/1987 | Silvestrini |
| 4,743,260 | A | 5/1988 | Burton |
| 4,772,286 | A | 9/1988 | Goble et al. |
| 4,773,402 | A | 9/1988 | Asher et al. |
| 4,776,851 | A | 10/1988 | Bruchman et al. |
| 4,794,916 | A | 1/1989 | Porterfield et al. |
| 4,870,957 | A | 10/1989 | Goble et al. |
| 4,955,910 | A | 9/1990 | Bolesky |
| 4,966,600 | A | 10/1990 | Songer et al. |
| 4,998,936 | A | 3/1991 | Mehdian |
| 5,002,574 | A | 3/1991 | May et al. |
| 5,011,484 | A | 4/1991 | Breard |
| 5,011,494 | A | 4/1991 | Von Recum et al. |
| 5,030,220 | A | 7/1991 | Howland |
| 5,092,866 | A | 3/1992 | Breard et al. |
| 5,108,433 | A | 4/1992 | May et al. |
| 5,116,340 | A | 5/1992 | Songer et al. |
| 5,171,280 | A | 12/1992 | Baumgartner |
| 5,180,393 | A | 1/1993 | Commarmond |
| 5,282,863 | A | 2/1994 | Burton |
| 5,354,917 | A | 10/1994 | Sanderson et al. |
| 5,366,455 | A | 11/1994 | Dove et al. |
| 5,387,213 | A | 2/1995 | Breard et al. |
| 5,395,374 | A | 3/1995 | Miller et al. |
| 5,415,658 | A | 5/1995 | Kilpela et al. |
| 5,415,661 | A | 5/1995 | Holmes |
| 5,449,361 | A | 9/1995 | Preissman |
| 5,456,722 | A | 10/1995 | McLeod et al. |
| 5,458,601 | A | 10/1995 | Young, Jr. et al. |
| 5,462,542 | A | 10/1995 | Alesi, Jr. |
| 5,496,318 | A | 3/1996 | Howland et al. |
| 5,540,698 | A | 7/1996 | Preissman |
| 5,562,653 | A | 10/1996 | Thompson |
| 5,562,737 | A | 10/1996 | Graf |
| 5,593,407 | A | 1/1997 | Reis |
| 5,609,634 | A | 3/1997 | Voydeville |
| 5,628,756 | A | 5/1997 | Barker, Jr. et al. |
| 5,645,084 | A | 7/1997 | McKay |
| 5,645,599 | A | 7/1997 | Samani |
| 5,669,917 | A | 9/1997 | Sauer et al. |
| 5,672,175 | A | 9/1997 | Martin |
| 5,707,379 | A | 1/1998 | Fleenor et al. |
| 5,725,582 | A | 3/1998 | Bevan et al. |
| 5,810,815 | A | 9/1998 | Morales |
| 5,836,948 | A | 11/1998 | Zucherman et al. |
| 5,902,305 | A | 5/1999 | Beger et al. |
| RE36,221 | E | 6/1999 | Breard et al. |
| 5,928,232 | A | 7/1999 | Howland et al. |
| 5,933,452 | A | 8/1999 | Eun |
| 5,935,133 | A | 8/1999 | Wagner et al. |
| 5,964,769 | A | 10/1999 | Wagner et al. |
| 5,989,256 | A | 11/1999 | Kuslich et al. |
| 6,053,921 | A | 4/2000 | Wagner et al. |
| 6,193,721 | B1 | 2/2001 | Michelson |
| 6,224,630 | B1 | 5/2001 | Bao et al. |
| 6,248,106 | B1 | 6/2001 | Ferree |
| 6,283,996 | B1 | 9/2001 | Chervitz et al. |
| 6,287,308 | B1 | 9/2001 | Betz et al. |
| 6,290,724 | B1 | 9/2001 | Marino |
| 6,296,643 | B1 | 10/2001 | Hopf et al. |
| 6,312,431 | B1 | 11/2001 | Asfora |
| 6,322,279 | B1 | 11/2001 | Yamamoto et al. |
| 6,364,883 | B1 | 4/2002 | Santilli |
| 6,378,289 | B1 | 4/2002 | Trudeau et al. |
| 6,391,030 | B1 | 5/2002 | Wagner et al. |
| 6,395,018 | B1 | 5/2002 | Castaneda |
| 6,419,677 | B2 | 7/2002 | Zucherman et al. |
| 6,427,080 | B1 | 7/2002 | Radak |
| 6,436,099 | B1 | 8/2002 | Drewry et al. |
| 6,451,019 | B1 | 9/2002 | Zucherman et al. |
| 6,468,309 | B1 | 10/2002 | Lieberman |
| 6,488,683 | B2 | 12/2002 | Lieberman |
| 6,517,578 | B2 | 2/2003 | Hein |
| 6,558,389 | B2 | 5/2003 | Clark et al. |
| 6,582,433 | B2 | 6/2003 | Yun |
| 6,589,246 | B1 | 7/2003 | Hack et al. |
| 6,605,091 | B1 | 8/2003 | Iwanski |
| 6,616,669 | B2 | 9/2003 | Ogilvie et al. |
| 6,626,944 | B1 | 9/2003 | Taylor |
| 6,629,975 | B1 | 10/2003 | Kilpela et al. |
| 6,652,527 | B2 | 11/2003 | Zucherman et al. |
| 6,652,585 | B2 | 11/2003 | Lange |
| 6,656,185 | B2 | 12/2003 | Gleason et al. |
| 6,669,729 | B2 | 12/2003 | Chin |
| 6,682,533 | B1 | 1/2004 | Dinsdale et al. |
| 6,689,140 | B2 | 2/2004 | Cohen |
| 6,689,168 | B2 | 2/2004 | Lieberman |
| 6,695,852 | B2 | 2/2004 | Gleason |
| 6,712,819 | B2 | 3/2004 | Zucherman et al. |
| 6,716,245 | B2 | 4/2004 | Pasquet et al. |
| 6,761,720 | B1 | 7/2004 | Senegas |
| 6,828,357 | B1 | 12/2004 | Martin et al. |
| 6,835,205 | B2 | 12/2004 | Atkinson et al. |
| 6,899,716 | B2 | 5/2005 | Cragg et al. |
| 6,989,011 | B2 | 1/2006 | Paul et al. |
| 7,029,475 | B2 | 4/2006 | Panjabi |
| 7,163,558 | B2 | 1/2007 | Senegas et al. |
| 7,201,751 | B2 | 4/2007 | Zucherman et al. |
| 7,229,441 | B2 * | 6/2007 | Trieu ............... A61B 17/7022 606/279 |
| 7,335,203 | B2 | 2/2008 | Winslow et al. |
| 7,413,576 | B2 | 8/2008 | Sybert et al. |
| 7,452,351 | B2 | 11/2008 | Miller et al. |
| 7,458,981 | B2 | 12/2008 | Fielding et al. |
| 7,520,887 | B2 * | 4/2009 | Maxy ............... A61B 17/7062 606/248 |
| 7,524,324 | B2 | 4/2009 | Winslow |
| 7,553,320 | B2 | 6/2009 | Molz, IV et al. |
| 7,591,837 | B2 | 9/2009 | Goldsmith |
| 7,909,853 | B2 | 3/2011 | Zucherman et al. |
| 8,029,541 | B2 | 10/2011 | Alamin et al. |
| 8,029,549 | B2 | 10/2011 | Malandain et al. |
| 8,162,982 | B2 | 4/2012 | Alamin et al. |
| 8,187,307 | B2 | 5/2012 | Alamin et al. |
| 8,486,110 | B2 | 7/2013 | Fielding et al. |
| 8,529,606 | B2 | 9/2013 | Alamin et al. |
| 8,790,372 | B2 | 7/2014 | Alamin et al. |

(56) References Cited

U.S. PATENT DOCUMENTS

| | | | |
|---|---|---|---|
| 8,920,473 B2* | 12/2014 | Trautwein | A61B 17/1757 606/246 |
| 9,149,304 B2 | 10/2015 | Alamin et al. | |
| 2001/0007073 A1 | 7/2001 | Zucherman et al. | |
| 2002/0095154 A1 | 7/2002 | Atkinson et al. | |
| 2002/0147449 A1 | 10/2002 | Yun | |
| 2002/0151978 A1 | 10/2002 | Zacouto et al. | |
| 2002/0161446 A1 | 10/2002 | Bryan et al. | |
| 2003/0023241 A1 | 1/2003 | Drewry et al. | |
| 2003/0050700 A1 | 3/2003 | Kihara | |
| 2003/0088251 A1 | 5/2003 | Braun et al. | |
| 2003/0153914 A1 | 8/2003 | Oribe et al. | |
| 2004/0024458 A1 | 2/2004 | Senegas et al. | |
| 2004/0034351 A1 | 2/2004 | Sherman et al. | |
| 2004/0082954 A1 | 4/2004 | Teitelbaum et al. | |
| 2004/0106995 A1 | 6/2004 | Le Couedic et al. | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0143268 A1 | 7/2004 | Falahee | |
| 2004/0167520 A1 | 8/2004 | Zucherman et al. | |
| 2004/0172132 A1 | 9/2004 | Ginn | |
| 2004/0215341 A1 | 10/2004 | Sybert et al. | |
| 2004/0243239 A1 | 12/2004 | Taylor | |
| 2005/0033435 A1 | 2/2005 | Belliard et al. | |
| 2005/0049708 A1 | 3/2005 | Atkinson et al. | |
| 2005/0123581 A1 | 6/2005 | Ringeisen et al. | |
| 2005/0131405 A1 | 6/2005 | Molz, IV et al. | |
| 2005/0154390 A1 | 7/2005 | Biedermann et al. | |
| 2005/0192581 A1 | 9/2005 | Molz et al. | |
| 2005/0203514 A1* | 9/2005 | Jahng | A61B 17/1757 606/263 |
| 2005/0203624 A1 | 9/2005 | Serhan et al. | |
| 2005/0216017 A1 | 9/2005 | Fielding | |
| 2005/0228383 A1 | 10/2005 | Zucherman et al. | |
| 2005/0267470 A1 | 12/2005 | McBride | |
| 2005/0267518 A1 | 12/2005 | Wright et al. | |
| 2006/0036324 A1 | 2/2006 | Sachs et al. | |
| 2006/0041259 A1 | 2/2006 | Paul et al. | |
| 2006/0064166 A1 | 3/2006 | Zucherman et al. | |
| 2006/0069447 A1 | 3/2006 | Disilvestro et al. | |
| 2006/0084976 A1 | 4/2006 | Borgstrom et al. | |
| 2006/0106381 A1 | 5/2006 | Ferree et al. | |
| 2006/0106397 A1 | 5/2006 | Lins | |
| 2006/0136060 A1 | 6/2006 | Taylor | |
| 2006/0142760 A1 | 6/2006 | McDonnell | |
| 2006/0149230 A1 | 7/2006 | Kwak et al. | |
| 2006/0195102 A1 | 8/2006 | Malandain | |
| 2006/0217726 A1 | 9/2006 | Maxy et al. | |
| 2006/0240533 A1 | 10/2006 | Sengupta et al. | |
| 2006/0241591 A1 | 10/2006 | Biscup et al. | |
| 2006/0241610 A1 | 10/2006 | Lim et al. | |
| 2006/0241614 A1* | 10/2006 | Bruneau | A61B 17/7062 606/249 |
| 2006/0271055 A1* | 11/2006 | Thramann | A61B 17/7053 606/74 |
| 2007/0010822 A1 | 1/2007 | Zalenski et al. | |
| 2007/0073293 A1 | 3/2007 | Martz et al. | |
| 2007/0083200 A1 | 4/2007 | Gittings et al. | |
| 2007/0173818 A1 | 7/2007 | Hestad et al. | |
| 2007/0213829 A1 | 9/2007 | Le Couedic et al. | |
| 2007/0233096 A1 | 10/2007 | Garcia-Bengochea | |
| 2007/0270827 A1* | 11/2007 | Lim | A61B 17/7062 606/86 A |
| 2007/0270828 A1 | 11/2007 | Bruneau et al. | |
| 2007/0299445 A1 | 12/2007 | Shadduck et al. | |
| 2008/0009866 A1 | 1/2008 | Alamin et al. | |
| 2008/0021466 A1 | 1/2008 | Shadduck et al. | |
| 2008/0027435 A1 | 1/2008 | Zucherman et al. | |
| 2008/0033552 A1 | 2/2008 | Lee et al. | |
| 2008/0045949 A1 | 2/2008 | Hunt et al. | |
| 2008/0051784 A1 | 2/2008 | Gollogly | |
| 2008/0097431 A1 | 4/2008 | Vessa | |
| 2008/0108993 A1 | 5/2008 | Bennett et al. | |
| 2008/0114357 A1 | 5/2008 | Allard et al. | |
| 2008/0125780 A1 | 5/2008 | Ferree | |
| 2008/0177298 A1 | 7/2008 | Zucherman et al. | |
| 2008/0183209 A1 | 7/2008 | Robinson et al. | |
| 2008/0234736 A1* | 9/2008 | Trieu | A61B 17/7026 606/250 |
| 2008/0262549 A1 | 10/2008 | Bennett et al. | |
| 2008/0281423 A1 | 11/2008 | Sheffer et al. | |
| 2008/0294200 A1* | 11/2008 | Kohm | A61B 17/7062 606/279 |
| 2008/0312693 A1 | 12/2008 | Trautwein et al. | |
| 2008/0319487 A1 | 12/2008 | Fielding et al. | |
| 2009/0030457 A1 | 1/2009 | Janowski et al. | |
| 2009/0082820 A1 | 3/2009 | Fielding et al. | |
| 2009/0118766 A1 | 5/2009 | Park et al. | |
| 2009/0182296 A1 | 7/2009 | Dennis | |
| 2009/0198282 A1 | 8/2009 | Fielding et al. | |
| 2009/0264929 A1 | 10/2009 | Alamin et al. | |
| 2009/0264932 A1 | 10/2009 | Alamin et al. | |
| 2009/0270918 A1 | 10/2009 | Attia et al. | |
| 2009/0292314 A1* | 11/2009 | Mangione | A61B 17/7062 606/249 |
| 2010/0004701 A1 | 1/2010 | Malandain et al. | |
| 2010/0023060 A1 | 1/2010 | Bennett et al. | |
| 2010/0036424 A1 | 2/2010 | Fielding et al. | |
| 2010/0234890 A1 | 9/2010 | Alamin et al. | |
| 2010/0234894 A1 | 9/2010 | Alamin et al. | |
| 2010/0249839 A1 | 9/2010 | Alamin et al. | |
| 2010/0274285 A1* | 10/2010 | Rouleau | A61B 17/7007 606/246 |
| 2011/0238114 A1* | 9/2011 | Lim | A61B 17/7065 606/248 |
| 2011/0295318 A1 | 12/2011 | Alamin et al. | |
| 2012/0165872 A1 | 6/2012 | Alamin et al. | |
| 2012/0184998 A1 | 7/2012 | Alamin et al. | |
| 2012/0209328 A1 | 8/2012 | Alamin et al. | |
| 2013/0317553 A1 | 11/2013 | Alamin et al. | |

FOREIGN PATENT DOCUMENTS

| | | | |
|---|---|---|---|
| EP | 0743045 A3 | 12/1996 | |
| EP | 0873718 A2 | 10/1998 | |
| EP | 1994901 A1 | 11/2008 | |
| FR | 2681525 A1 | 3/1993 | |
| FR | 2693364 A1 | 1/1994 | |
| FR | 2703239 A1 | 10/1994 | |
| FR | 2704745 A1 | 11/1994 | |
| FR | 2714591 A1 | 7/1995 | |
| FR | 2717675 A1 | 9/1995 | |
| FR | 2722980 A1 | 2/1996 | |
| FR | 2828398 A1 | 2/2003 | |
| FR | 2844179 A1 | 3/2004 | |
| FR | 2851154 A1 | 8/2004 | |
| FR | 2874167 A1 | 2/2006 | |
| FR | 2884136 A1 | 10/2006 | |
| JP | 2001-507599 A | 6/2001 | |
| JP | 2003523784 A | 8/2003 | |
| JP | 2004502490 A | 1/2004 | |
| JP | 2004527287 A | 9/2004 | |
| WO | WO 99/42051 A1 | 8/1999 | |
| WO | WO 01/28442 A1 | 4/2001 | |
| WO | WO 02/03882 A2 | 1/2002 | |
| WO | WO 02/03882 A3 | 5/2002 | |
| WO | WO 02/051326 A1 | 7/2002 | |
| WO | WO 02/071960 A1 | 9/2002 | |
| WO | WO 03/045262 A2 | 6/2003 | |
| WO | WO 03/045262 A3 | 1/2004 | |
| WO | WO 2004/052246 A1 | 6/2004 | |
| WO | WO 2004/073532 A1 | 9/2004 | |
| WO | WO 2004/073533 A1 | 9/2004 | |
| WO | WO 2005/037150 A1 | 4/2005 | |
| WO | WO 2005/110258 A1 | 11/2005 | |
| WO | WO 2005/112835 A2 | 12/2005 | |
| WO | WO 2006/034423 A2 | 3/2006 | |
| WO | WO 2006/034423 A3 | 6/2006 | |
| WO | WO 2005/112835 A3 | 2/2007 | |
| WO | WO 2008/051423 A1 | 5/2008 | |
| WO | WO 2008/051801 A2 | 5/2008 | |
| WO | WO 2008/051802 A2 | 5/2008 | |
| WO | WO 2008/051806 A2 | 5/2008 | |

(56) References Cited

FOREIGN PATENT DOCUMENTS

| WO | WO 2008/051802 A3 | 7/2008 |
|---|---|---|
| WO | WO 2008/051806 A3 | 7/2008 |
| WO | WO 2008/051801 A3 | 8/2008 |
| WO | WO 2009/149407 A1 | 12/2009 |
| WO | WO 2010/028165 A1 | 3/2010 |
| WO | WO 2010/028165 A8 | 10/2010 |
| WO | WO 2009/149407 A9 | 2/2011 |

OTHER PUBLICATIONS

Office action dated Jul. 14, 2014 for U.S. Appl. No. 13/958,323.
Office action dated Sep. 30, 2014 for U.S. Appl. No. 13/274,171.
European search report dated May 10, 2013 for EP Application No. 07854186.9.
Abbott Spine. Wallis surgical technique. Product brochure. Apr. 2006. 1-24.
Al Baz, et al. Modified technique of tension band wiring in flexion injuries of the middle and lower cervical spine. Spine (Phila Pa 1976). Jun. 1, 1995;20(11):1241-4.
Brinckmann, et al. Mechanical aspects of lumber spine in musculoskeletal biomechanics. 2002; ch 11: 105-128.
Dickman, et al. Comparative mechanical properties of spinal cable and wire fixation systems. Spine (Phila Pa 1976). Mar. 15, 1997;22(6):596-604.
European office action dated Feb. 4, 2011 for EP Application No. 07863431.8.
European office action dated Jun. 4, 2010 for EP Application No. 07852824.7.
European office action dated Jun. 4, 2010 for EP Application No. 07863431.8.
European office action dated Oct. 5, 2009 for EP Application No. 07852824.7.
European search report and search opinion dated Oct. 13, 2009 for EP Application No. 07863431.8.
European search report dated Dec. 4, 2012 for EP Application No. 07844408.0.
European search report dated Dec. 6, 2012 for EP Application No. 10765340.4.
Frymoyer, et al. An overview of the incidences and costs of low back pain. Orthop Clin North Am. Apr. 1991;22(2):263-71.
Garner, et al. Development and preclinical testing of a new tension-band device for the spine: the Loop system. Eur Spine J. Oct. 2002;11 Suppl 2:S186-91.
Hamblen. Symposium Dynamic stabilization of the lumbar spine. Orthopaedics today international. Mar. 2006; 9:3. orthosupersite.com/view.asp?rID=6932.
Heller, et al. Stability of different wiring techniques in segmental spinal instrumentation. An experimental study. Arch Orthop Trauma Surg. 1998;117(1-2):96-9.
International search report and written opinion dated Mar. 14, 2008 for PCT/US2007/022191.
International search report and written opinion dated Mar. 24, 2008 for PCT/US2007/081835.
International search report and written opinion dated May 8, 2008 for PCT/US2007/081822.
International search report and written opinion dated Jun. 18, 2010 for PCT/US2010/031615.
International search report and written opinion dated Jun. 23, 2008 for PCT/US2007/081815.
International search report and written opinion dated Jul. 8, 2010 for PCT/US2010/031471.
Leahy, et al. Design of spinous process hooks for flexible fixation of the lumbar spine. Proc Inst Mech Eng H. 2000;214(5):479-87.
Leahy, et al. Mechanical testing of a flexible fixation device for the lumbar spine. Proc Inst Mech Eng H. 2000;214(5):489-95.
Medtronic Sofamor Dane USA, Inc. DIAM system implant. Product brochure. 2006. 1-20. spineinfo.ru/~files/DIAMST.pdf.
Minns, et al. Preliminary design and experimental studies of a novel soft implant for correcting sagittal plane instability in the lumbar spine. Spine (Phila Pa 1976). Aug. 15, 1997;22(16):1819-25.
Miyasaka, et al. Radiographic analysis of lumbar motion in relation to lumbosacral stability. Investigation of moderate and maximum motion. Spine (Phila Pa 1976). Mar. 15, 2000;25(6):732-7.
Moll, et al. Normal range of spinal mobility. Ann. Rheum. Dis. 1971; 30:381-386.
Office action dated Jan. 20, 2012 for U.S. Appl. No. 12/106,049.
Office action dated Jan. 29, 2013 for U.S. Appl. No. 11/827,980.
Office action dated Mar. 5, 2013 for U.S. Appl. No. 13/455,917.
Office action dated Mar. 19, 2013 for U.S. Appl. No. 12/106,049.
Office action dated Apr. 20, 2010 for U.S. Appl. No. 11/777,366.
Office action dated Apr. 24, 2012 for U.S. Appl. No. 11/875,674.
Office action dated May 10, 2011 for U.S. Appl. No. 11/827,980.
Office action dated May 13, 2011 for U.S. Appl. No. 12/426,167.
Office action dated May 31, 2012 for U.S. Appl. No. 13/206,339.
Office action dated Jun. 10, 2011 for U.S. Appl. No. 11/875,674.
Office action dated Jun. 13, 2011 for U.S. Appl. No. 12/426,119.
Office action dated Jun. 19, 2012 for U.S. Appl. No. 11/875,674.
Office action dated Aug. 2, 2012 for U.S. Appl. No. 11/827,980.
Office action dated Aug. 5, 2011 for U.S. Appl. No. 12/106,049.
Office action dated Oct. 2, 2012 for U.S. Appl. No. 12/106,049.
Office action dated Oct. 4, 2011 for U.S. Appl. No. 11/875,674.
Office action dated Oct. 12, 2010 for U.S. Appl. No. 11/777,366.
Office action dated Oct. 17, 2011 for U.S. Appl. No. 12/426,167.
Office action dated Oct. 23, 2012 for U.S. Appl. No. 11/875,674.
Office action dated Oct. 29, 2012 for U.S. Appl. No. 13/455,917.
Office action dated Oct. 31, 2012 for U.S. Appl. No. 13/206,339.
Office action dated Dec. 1, 2010 for U.S. Appl. No. 11/827,980.
Papp, et al. An in vitro study of the biomechanical effects of flexible stabilization on the lumbar spine. Spine (Phila Pa 1976). Jan. 15, 1997;22(2):151-5.
Shephard, et al. Slippage of a spinous process hook during flexion in a flexible fixation system for the lumbar spine. Med Eng Phys. Mar. 2001;23(2):135-41.
Shephard, et al. Spinous process strength. Spine (Phila Pa 1976). Feb. 1, 2000;25(3):319-23.
Voydeville, et al. Ligamentoplastie intervertebrate avec cale souple dans les instabilities lombaries. Intervertebral ligamentoplasty with flexible wedge in lumber instability. Orthop Traumatol. 1992; 2:259-264.
Co-pending U.S. Appl. No. 14/673,546, filed Mar. 30, 2015.
Notice of allowance dated Jan. 25, 2012 for U.S. Appl. No. 12/426,167.
Notice of allowance dated Feb. 5, 2013 for U.S. Appl. No. 13/206,339.
Notice of allowance dated Apr. 19, 2013 for U.S. Appl. No. 13/206,339.
Notice of allowance dated May 5, 2011 for U.S. Appl. No. 11/777,366.
Notice of allowance dated May 13, 2013 for U.S. Appl. No. 11/827,980.
Notice of allowance dated May 28, 2015 for U.S. Appl. No. 13/958,323.
Notice of allowance dated Jun. 10, 2014 for U.S. Appl. No. 13/427,551.
Notice of allowance dated Dec. 27, 2011 for U.S. Appl. No. 12/426,119.
Office action dated Nov. 13, 2014 for U.S. Appl. No. 13/958,323.
White; et al., Clinical biomechanics of the spine. vol. 2. Philadelphia: Lippincott, 1990.
Co-pending U.S. Appl. No. 14/875,495, filed Oct. 5, 2015.

* cited by examiner

METHODS AND SYSTEMS FOR LATERALLY
STABILIZED CONSTRAINT OF SPINOUS
PROCESSES

CROSS-REFERENCE TO RELATED APPLICATIONS

This application is a continuation of U.S. patent application Ser. No. 13/206,339 filed Oct. 14, 2011, which is a divisional of U.S. patent application Ser. No. 11/777,366 filed Jul. 13, 2007 now U.S. Pat. No. 8,029,541, which is a non-provisional of, and claims the benefit of prior U.S. Provisional Application No. 60/862,085, filed on Oct. 19, 2006; the present application is also a continuation in part of U.S. patent application Ser. No. 13/455,917 filed Apr. 25, 2012, which is a divisional of U.S. patent application Ser. No. 12/426,167, filed on Apr. 17, 2009, which is a continuation-in-part of PCT Application US2007/081815, filed on Oct. 18, 2007, which claims the benefit of Provisional Application No. 60/862,085, filed on Oct. 19, 2006; the present application is also a continuation in part of U.S. patent application Ser. No. 13/427,551 filed Mar. 22, 2012, which is a divisional of and claims the benefit of U.S. patent application Ser. No. 12/426,119 filed Apr. 17, 2009, which is a continuation-in-part of and claims priority to International PCT Application No. PCT/US2007/081822 filed Oct. 18, 2007, which claims priority to U.S. Provisional Patent Application No. 60/862,085 filed Oct. 19, 2006; U.S. patent application Ser. No. 12/426,119 also is a non-provisional of, and claims the benefit of U.S. Provisional Patent Application No. 61/158,892 filed Mar. 10, 2009; the present application is also a continuation in part of U.S. patent application Ser. No. 13/274,171 filed Oct. 14, 2011, which is continuation of International PCT Application No. PCT/US2010/031471 filed Apr. 16, 2010, which claims priority to U.S. patent application Ser. No. 12/426,119 filed Apr. 17, 2009, which is a continuation-in-part of International Patent Application No. PCT/US2007/081822 filed Oct. 18, 2007, which claims priority to U.S. Provisional Patent Application No. 60/862,085 filed Oct. 19, 2006; U.S. patent application Ser. No. 12/426,119 is also a non-provisional of, and claims the benefit of U.S. Provisional Patent Application No. 61/158,892 filed Mar. 10, 2009; the present application is also a continuation in part of U.S. patent application Ser. No. 12/106,049 filed Apr. 18, 2008, which is a continuation in part of U.S. patent application Ser. No. 11/875,674 filed Oct. 19, 2007, which is a non-provisional of, and claims the benefit of U.S. Provisional Patent Application No. 60/862,085 filed Oct. 19, 2006; the entire contents of each of the above is incorporated herein by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

Figure 1:
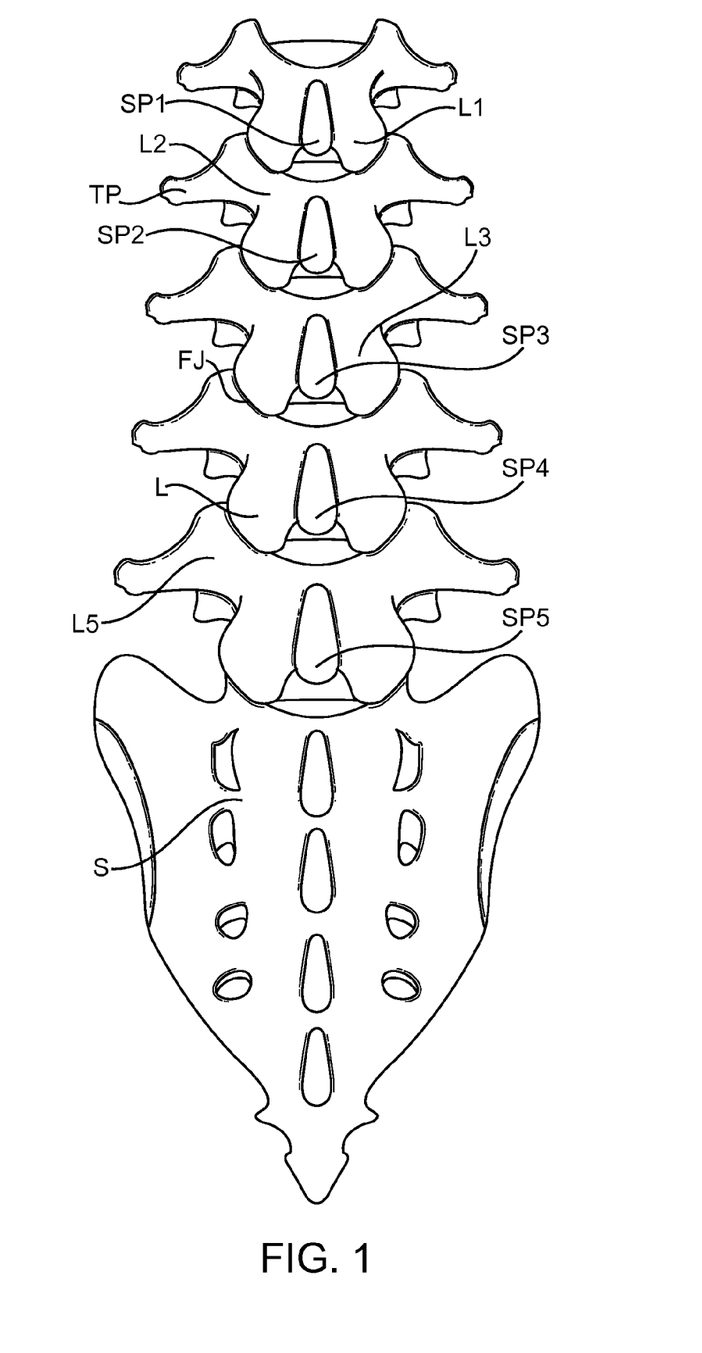
FIG. 1 is a schematic diagram illustrating the lumbar region of the spine including the spinal processes (SP), facet joints (FJ), lamina (L), transverse processes (TP), and sacrum (S).

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine (FIG. 1). Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients, can dramatically affect their ability to work and otherwise enjoy their lives.

This pain experienced by patients with discogenic low back pain can be thought of as flexion instability and is related to flexion instability that is manifested in other conditions. The most prevalent of these is spondylolisthesis, a spinal condition in which abnormal segmental translation is exacerbated by segmental flexion.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebrae. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinal processes and provides an elastic restraint to the spreading apart of the spinal processes which occurs during flexion. Such devices and methods for their use are described in U.S. Patent Application 2005/02161017A1, published on Sep. 29, 2005, and having common inventors with the present application.

Figure 2:
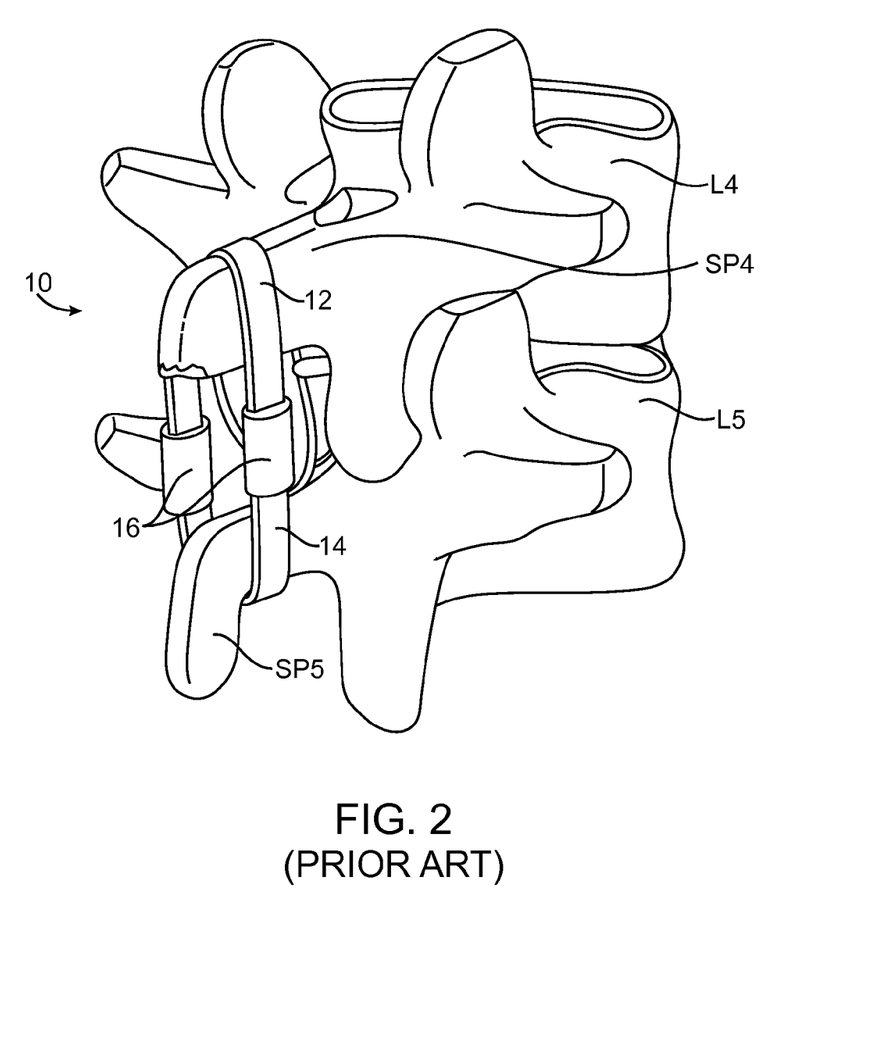
FIG. 2 illustrates a spinal implant of the type described in US 2005/0216017A1.

As illustrated in FIG. 2, an implant 10 as described in the '017 application, typically comprises an upper strap component 12 and a lower strap component 14 joined by a pair of compliant members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring of rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinal processes which provides a force that resists flexion. The force increases, typically linearly with a non-variable spring constant, as the processes move further apart. Usually, the straps themselves will be essentially non-compliant so that the degree of elasticity or compliance may be controlled and provided solely by the compliance members 16.

Figure 3:
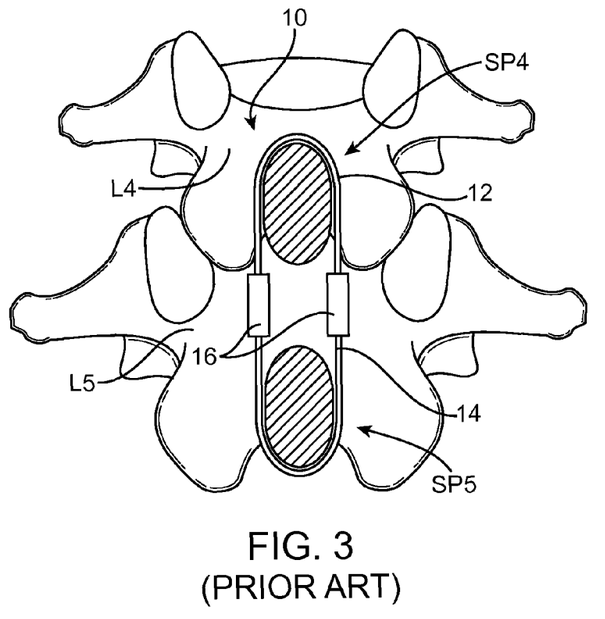
FIGS. 3 and 4 illustrate how the spinal implant of FIG. 2 can become misaligned over time.
Figure 4:
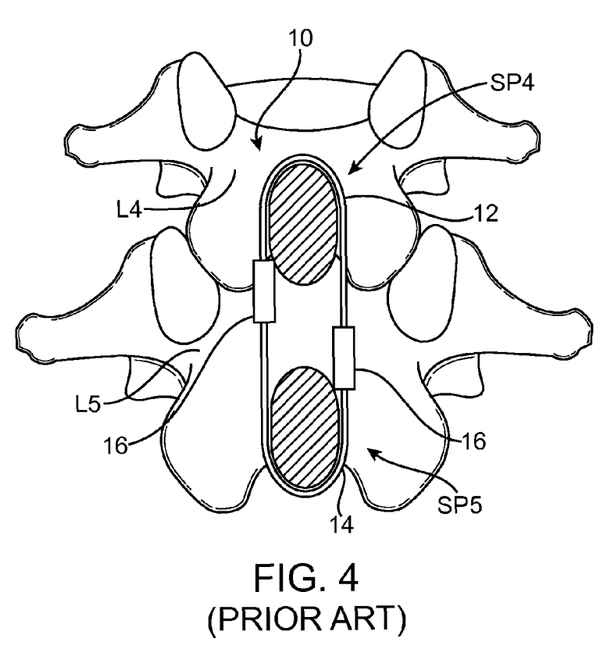

Ideally, the compliance members 16 will remain horizontally aligned and spaced generally between the spinous processes SP4 and SP5, as shown generally in FIG. 3. In some instances, however, the desired symmetry may be lost if the implant structure 10 becomes circumferentially displaced about the spinous processes SP4 and SP5, as shown in FIG. 4. Such displacement can affect the ability of the implant to provide a uniform, symmetric elastic force to inhibit flexion of the spinous processes in accordance with the desired treatment.

For these reasons, it would be desirable to provide improved spinal implants and methods for their use in inhibiting flexion in patients suffering from discogenic pain. It would be particularly desirable if the improved devices would provide the desired elastic forces to the spinous processes without displacement or loss of symmetry of the device over time. At least some of these objectives will be met by the inventions described hereinbelow.

2. Description of the Background Art

US 2005/0216017A1 has been described above. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. US 2002/0151978; US 2004/0024458; US 2004/0106995; US 2004/0116927; US 2004/0117017; US 2004/0127989; US 2004/0172132; US 2005/0033435; US 2005/0049708; US 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

SUMMARY OF THE INVENTION

The present invention provides spinal implants and methods for restricting spinal flexion for the treatment of discogenic pain and other spinal conditions, such as spondylolisthesis, where the physician desires to control spinal flexion. The spinal implants comprise a tether structure adapted to encircle at least two spinous processes, where at least a portion of the tether structure is adapted to elastically elongate to apply tension to the spinous processes as the spine undergoes flexion, i.e. as the spinous processes move apart as the patient leans forward. The tether structure may comprise any of the particular structures described in detail in U.S. patent application Ser. No. 11/076,469, filed on Mar. 9, 2005, and published as US 2005/0216017 A1, the full disclosure of which is incorporated herein by reference.

In particular, in the simplest embodiments, the tether structure may comprise a single, continuous loop of material wherein all or a portion of the loop is formed of a compliant material to provide the desired elasticity. More commonly, the tether structure will comprise one or more band segments joined by one or more compliance members, where the band(s) are typically non-distensible and the compliance member(s) provide for the desired elasticity. In some instances, the compliance members may comprise spring or other elements which provide an elastic tensioning force where the band member(s) are attached to opposite ends of the spring member. In other instances, the compliance members could include elastomeric or other compression elements, where the band member(s) are attached to opposed sides of the compressive elements so that the elasticity is provided by compression on the compression member.

In preferred embodiments, the tether structure will comprise a pair of band members joined by a pair of compliance members, where an upper band member will be placed over the superior surface of an upper spinous process and the lower band member will be placed over an inferior surface of the lower spinous process. The compliance members will be generally horizontally aligned across the region between the upper and lower spinous processes.

In a particular aspect of the present invention, the spinal implants will include at least one cross-member coupled to opposed portions of the tether structure, where the cross member is positioned to lie between the spinous processes when the tether structure encircles the processes as described above. In specific embodiments, the cross-member will extend between the horizontally aligned compliance members, but in other embodiments a cross-member could be coupled to other portions or components of the tether structure, including the band or loop elements which are disposed over the spinous processes.

The cross-member(s) functions to stabilize the tether structure after the tether structure has been implanted over the spinous processes. In particular, the cross-member(s) will help maintain the symmetry of the device so that it does not circumferentially rotate or migrate over the spinous processes, which is a potential problem when the tether includes one or more compliance members. In addition, the cross-member(s) may optionally maintain the lateral spacing between the two sides of the device, such as between a pair of horizontally aligned compliance members. The cross-member(s) may further prevent or inhibit vibration or sinusoidal movement of the device which may result from dynamic and/or cyclic loading.

In addition to the stabilization functions, a cross-member may help in initial placement and positioning of the tether structure. For example, a tether structure including a pair of horizontally aligned compliance members may be introduced and assembled in situ, where the cross-member helps establish the initial horizontal alignment between the compliance members. Alternatively, when no compliance members are to be used, the cross-member could itself provide for connection points for attaching upper and lower band segments. Additionally, the cross-member(s) can create pivot points to allow rotation or pivoting of the band relative to the cross-member(s) as well as the other band segments.

The cross-member(s) may have a wide variety of particular configurations. The most common cross-member(s) will have generally rigid structures, e.g. in the form of a rod, bar, beam, or the like. In other instances, however, the cross-member(s) may be relatively flexible, in some cases being in the form of a wire, ribbon, string, spring, suture, or the like. In still other configurations, the cross-member(s) may be linearly compressible, but not extensible, in order to allow for a controlled degree of inward motion of the tether structure after it has been placed. In still other configurations, the cross-member(s) may be linearly non-compressible, but allow for a small degree of axial extension in order to prevent inward motion or intrusion of the tether structure into the region between the spinous processes.

There are also a variety of ways in which the cross-member(s) may be attached to the tether structure. Typically, the cross-member(s) will be attached to opposed compliance members (usually to housings of the compliance member subassemblies as shown in the '017 application previously incorporated by reference), where the attachment can be rigid, semi-rigid, pivotal, or the like. In a first exemplary embodiment, the cross-member is rigidly attached to a pair of compliance members in a generally H-shaped configuration. In other instances, the connections may be pivotal or non-rigid, as mentioned above. Still further, the cross-member can be completely flexible which would allow for a small degree of motion between the compliance members after implantation.

While most embodiments of the present invention will employ only a single cross-member, in other embodiments two or more cross-members may be used. For example, a pair of cross-members may be positioned between opposed portions of the tether structure, where an upper cross-member is located immediately below the inferior surface of the upper spinal process, while the lower cross-member is positioned immediately adjacent to a superior surface of the lower spinal process. Alternatively, such cross-member pairs may be positioned more closely to the compliance members, e.g. where they lie immediately above and below the compliance members. In still other embodiments, the cross-members may be slidably attached to the bands or other portions of the tether structure so that the cross members may move in response to a force applied by the spinous processes or otherwise.

In all the embodiments of the present invention, it will be desirable that the cross-member(s) provide little or no resistance to extension, i.e. motion of the adjacent spinous processes toward one another. When the cross-member consists of a single rod, bar, structure, or other flexible element extending between exposed portions of the tether structure, the cross-member will usually have a very small vertical height (typically less than 6 mm, usually in the range from 1 mm to 3 mm), and it is unlikely that the cross-member would contact either spinous process even in an extreme degree of extension, so long as the cross-member is located at a position which is equally spaced apart from the two spinous processes. In other instances, however, the cross-member could have a larger cross-sectional profile which might contact either or both spinous processes as the spine undergoes extension. In such cases, it is desirable that the cross-member be collapsible or otherwise provide minimum force against either or both processes.

Usually, the cross-member will be implanted through the interspinous ligament which extends between the upper and lower spinous processes. In such instances, it is desirable that the cross-member itself have a relatively low profile to permit passage through the ligament with minimum trauma. Often, it will be desirable to have the cross-member detachable from at least one of the opposed tether structure components so that the cross-members or other portions of the tether structure do not need to be passed through the interspinous ligament.

In another aspect of the present invention, methods for stabilizing spinal flexion comprise positioning a continuous tether structure over a pair of adjacent spinous processes on adjacent vertebrae to elastically restrict flexion. The tether structure will be positioned and have mechanical properties which will elastically tension the processes when the processes are in flexion. In accordance with the principles of the present invention, opposed portions of the tether structure are mechanically coupled, usually through the interspinous ligament, in order to stabilize the structure, particularly to inhibit circumferential displacement of the tether structure over time.

In the exemplary embodiments, the opposed portions of the tether structure will comprise compliance members, and it will be the compliance members which are mechanically coupled to stabilize the structure in situ. Typically, the compliance members will be connected by at least one cross-member wherein said at least one cross-member is fixably or non-fixably attached to the compliance members. In some embodiments, one end of the cross-member may be fixably attached to one compliance member while the other member is non-fixably attached to the other compliance member. The cross-member itself may be rigid, semi-rigid, or non-rigid, and in all instances the cross-member will provide no significant inhibition of spinal extension. Preferably, the cross-member will pass through the interspinous ligament without significant damage or compromise to its integrity.

Optionally, one or more additional tether structures may be implanted around other pair(s) of spinous processes in the manner described above.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 14A and 14B illustrate use of a reinforcement member on a single connector which does not include a compliance member, while

DETAILED DESCRIPTION OF THE INVENTION

Figure 5:
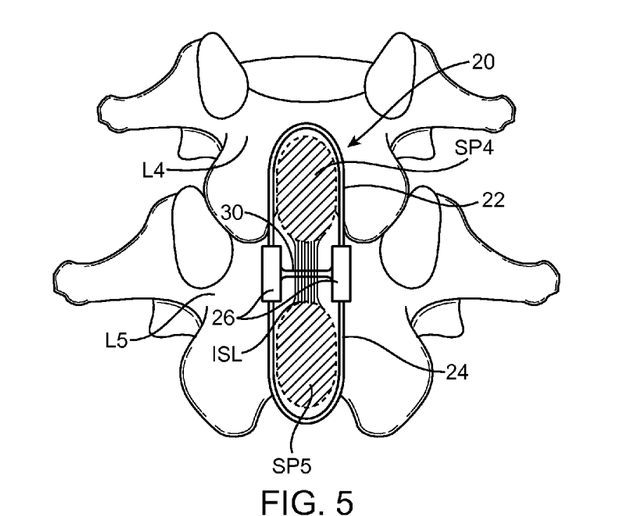
FIG. 5 illustrates a first embodiment of a spinal implant having a cross-member in accordance with the principles of the present invention.

Referring now to FIG. 5, a spinal implant 20 constructed in accordance with the principles of the present invention comprises an upper strap 22, a lower strap 24, and a pair of compliance members 26 joining the upper and lower straps. Typically, the upper and lower straps 22 and 24 will be non-distensible but will be joined to the compliance members 26 so that they can be expanded from a constricted configuration, as shown in broken line, when the patient's spine is in a neutral position between flexion and extension, to an expanded configuration (shown in full line) when the patient's spine is in flexion. The compliance members 26 will provide a force which acts against the extension of the spinous processes, as generally described in prior patent application U.S. 2005/0216017, which has been previously incorporated herein by reference. In particular accordance with the present invention, a cross-member 30 extends between and joins the compliance members 26. The cross-member 30 passes through the interspinous ligament ISL.

Figure 6A:
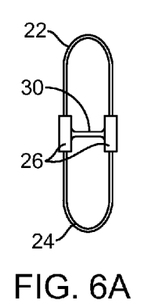
FIGS. 6A and 6B illustrate the spinal implant of FIG. 5 having a rigid cross-member.
Figure 6B:
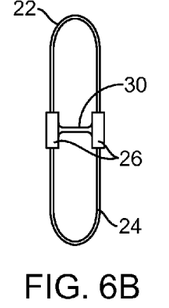
Figure 7A:
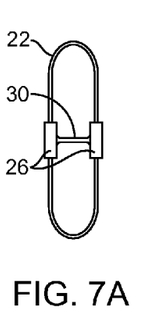
FIGS. 7A and 7B illustrate the spinal implant of FIG. 5 having a semi-rigid cross-member.
Figure 7B:
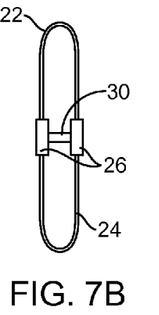
Figure 8A:
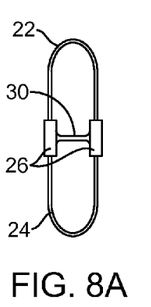
FIGS. 8A and 8B illustrate the cross-member of FIG. 5 having an elastic cross-member.
Figure 8B:
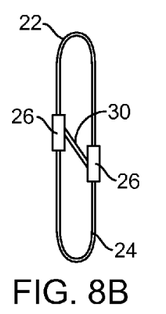

As shown in FIGS. 6A and 6B, the cross-member 30 may be rigid and be rigidly attached to the compliance members 26 in a generally H-shaped configuration so that the compliance members do not shift relative to each other even when the upper and lower bands 22 and 24 are pulled apart, as shown in FIG. 6B. Alternatively, the cross-member 30 may be semi-rigid (or semi-compliant) so that it will undergo compression when the upper band 22 is pulled away from the lower band 24, as shown in FIG. 7B. In a third embodiment, the cross-member 30 may be entirely elastic, as shown in FIGS. 8A and 8B. In such instances, the cross-member 30 will allow the compliance members 26 to vertically displaced relative to each other by a controlled amount, as shown in FIG. 8B.

Figure 9:
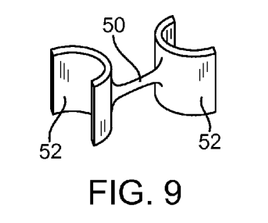
FIG. 9 illustrates a specific embodiment of a cross-member useful in the apparatus and methods of the present invention.
Figure 10:
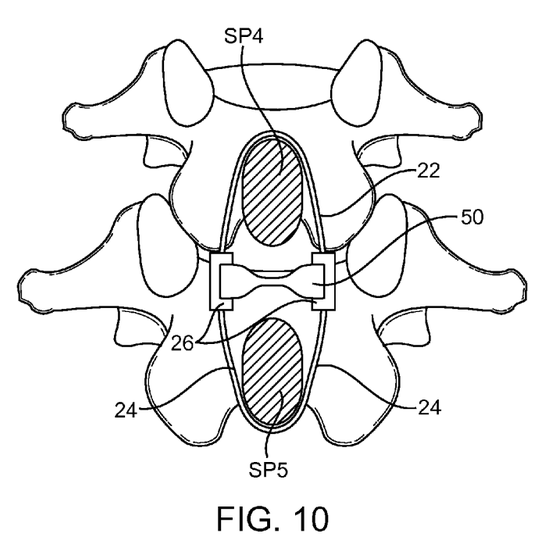
FIG. 10 illustrates the cross-member of FIG. 9 in an implant.

FIG. 9 illustrates an exemplary cross-member 50 which can be coupled to compliance members 26, as shown in FIG. 10. The cross-member 50 is a rigid structure which may be attached (and optionally detached) from the compliance member during implantation of the spinal implant. End portions 52 of the cross-member are shaped and adapted to be attached to the cylindrical bodies of the compliance members. Other shapes and structures for selective attachment and detachment of the cross-member are, of course, readily available.

Figure 11:
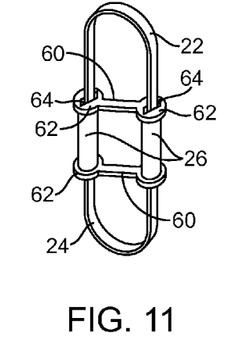
FIG. 11 illustrates an embodiment of the present invention having a pair of cross-members.
Figure 12:
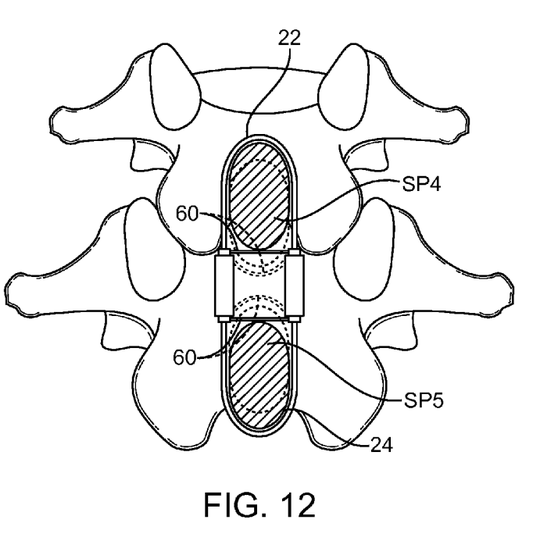
FIG. 12 illustrates the spinal implant of FIG. 11 in an implant.
Figure 13:
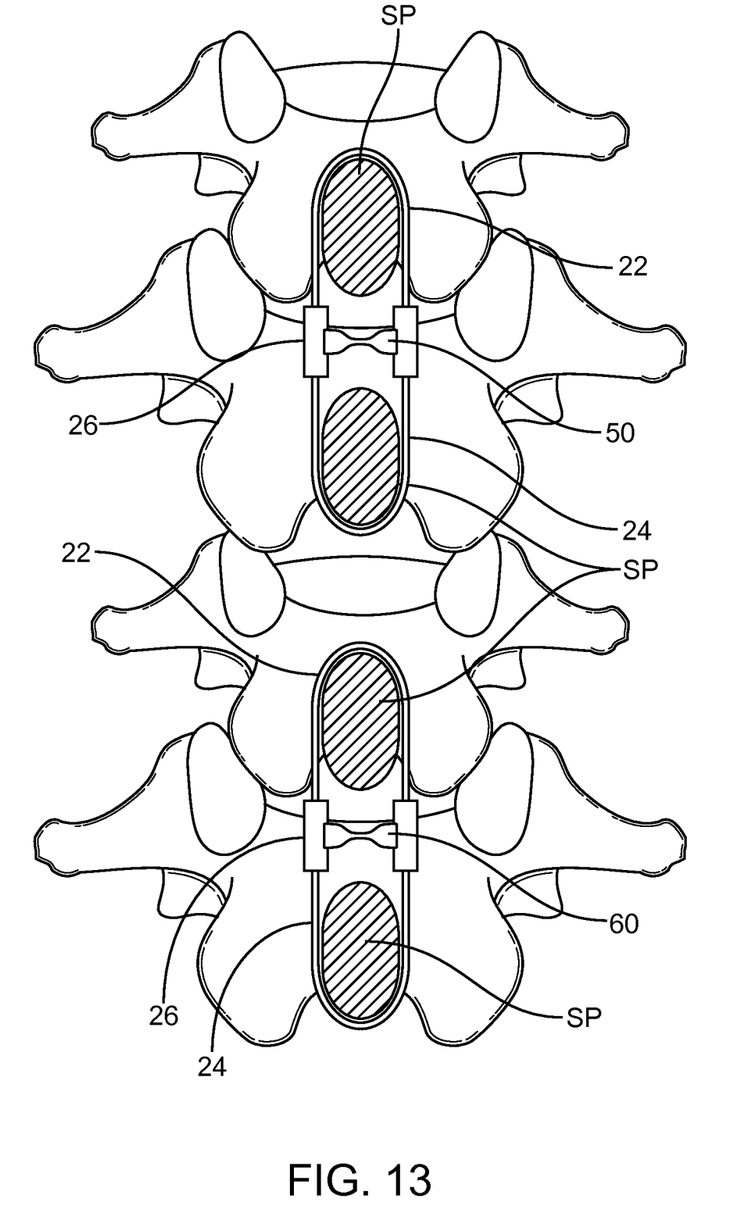
FIG. 13 illustrates an additional continuous tether structure over a spinous process on another pair of adjacent vertebrae.

A pair of cross-members 60 are illustrated in FIG. 11. The cross-members 60 have endpieces 62, each having a slot 64 which receives the corresponding band 22 or 24. Cross-members 60 can thus be disposed directly over the upper and lower surfaces of the compliance members 26, as shown in FIG. 12. Usually, cross-members 60 will themselves be compliant in order to avoid inhibiting of extension of the spinal processes SP4 and SP5, as shown in broken line in FIG. 12. FIG. 13 illustrates positioning at least one additional continuous tether structure over a spinous process on another pair of adjacent vertebrae, and mechanically coupling opposed portions of the at least one additional tether structure through the interspinous space.

Further details and alternative embodiments of flexion limiting devices, their use, and associated instruments are disclosed in the patent applications previously incorporated herein by reference.

Figure 14A:
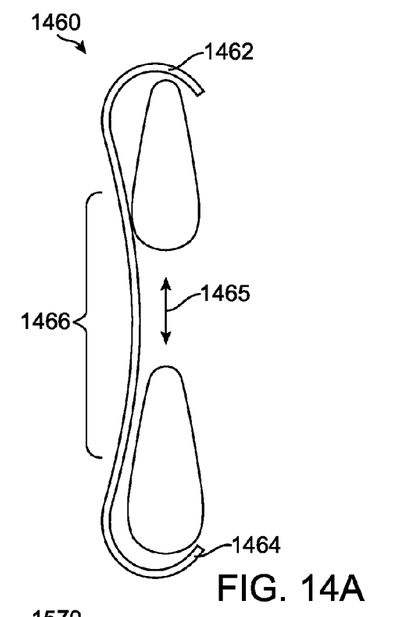

Referring now to FIG. 14, yet another spinous process constraint system 1460 comprises first and second hook-like attachment members 1462 and 1464. The hook members 1462 and 1464 are connected in a C-shaped pattern, as shown in FIG. 14.

Figure 14B:
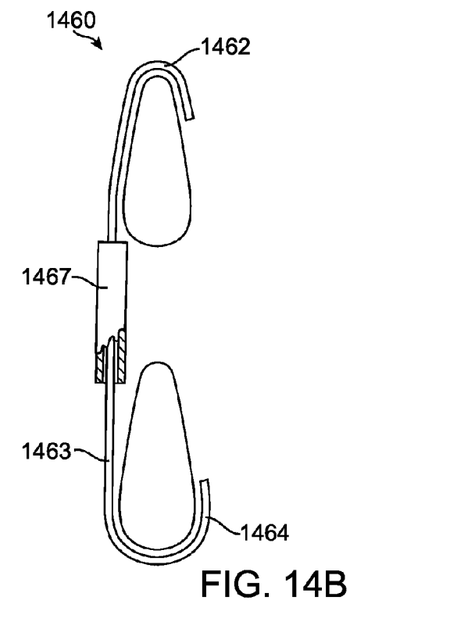

The spinous process constraint 1460 of FIG. 14 will have a tendency to deform when placed under an axial load as the spinous processes undergo a flexion causing movement in the direction of arrow 1465. Typically, a region 1466 of the constraint will tend to bow inwardly which causes the superior and inferior hook members 1462 and 1464 to displace laterally, increasing the risk that they will shift from their intended positions on the spinous processes. In order to alleviate this condition, a reinforcement member 1467 can be placed over a portion of the single connector 1463 between the hooks 1462 and 1464. The reinforcement member may be a simple sleeve constructed from a relatively rigid material, such as a metal or rigid polymer, having a central passage which is placed over the single connector. Other reinforcement structures would also be possible. Additionally, the sleeve embodiment shown in FIG. 14B could be modified to be used with constraint embodiments including compliance members as described elsewhere in this application.

Similarly, as shown in FIG. 15, a spinous process constraint system 1570 comprises first and second hook-like attachment members 1572 and 1574 arranged in C-shaped pattern, generally as shown in FIG. 14, and further comprises compliance member 1578 attached to superior and inferior segments of the single connector 1576 (which is preferably non-compliant).

Figure 15A:
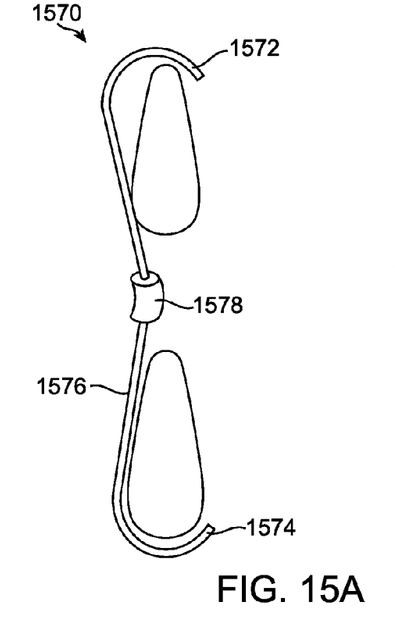
FIGS. 15A and 15B illustrate use of a reinforcement member on a single connector which includes a compliance member.
Figure 15B:
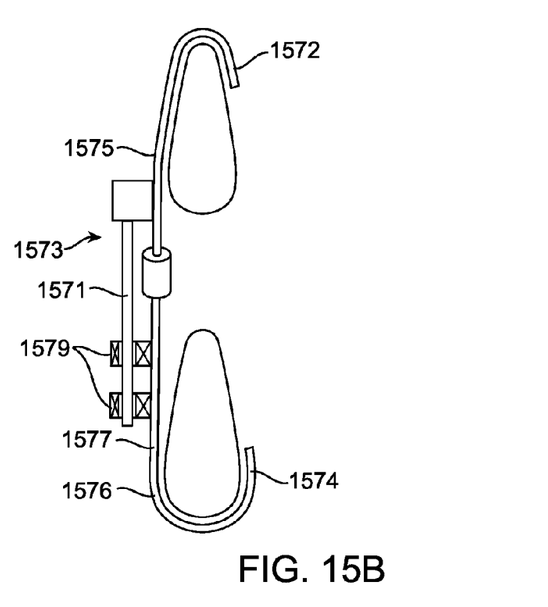

The spinous process constraint 1570 of FIG. 15 can also undergo deformation when subjected to an axial load, as shown in FIG. 15A. A reinforcement assembly 1573 specifically adapted for constraints having compliance members 1578 is illustrated in FIG. 15B. The reinforcement assembly 1573 connects to a superior segment 1575 of the single connector 1576 and includes a slide rod 1571 extending toward an inferior segment 1577 of the single connector 1576. The slide rod 1571 is received in a bearing structure 1579 attached to the interior segment 1577 which allows the rod to translate as the segments 1573 and 1577 move toward and away from each other as the spine undergoes extension and flexion. The reinforcement assembly 1571 helps maintain the proper alignment between the superior and inferior segments 1575 and 1577 to prevent the bowing and deformation illustrated in FIG. 15A.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for restricting flexion of a spinal segment having a spinal midline, said method comprising:
    providing a first attachment element and a second attachment element, wherein the first attachment element is joined to the second attachment element with one connector extending therebetween and wherein the one connector has an elastic stiffness in tension that resists flexion of the spinal segment without resisting extension thereof, wherein the one connector provides the elastic stiffness in tension between the attachment elements in the range from 7.5 N/mm to 50 N/mm;
    engaging the first attachment element to a first spinous process;
    engaging the second attachment element to a second spinous process or a sacrum;
    disposing the one connector beside one side of the spinal midline; and
    providing a reinforcement member that limits deformation of the one connector under an axial load, wherein the reinforcement member is coupled to the one connector.

2. The method of claim 1, wherein the elastic stiffness in tension is in the range from 10 N/mm to 25 N/mm.

3. The method of claim 2, wherein the elastic stiffness in tension is in the range from 10 N/mm to 15 N/mm.

4. The method claim 1, wherein the one connector provides an elastic stiffness in compression between the attachment elements below 3 N/mm.

5. The method of claim 4, wherein the elastic stiffness in compression is below 0.5 N/mm.

6. The method of claim 1, further comprising percutaneously introducing the attachment elements and the one connector.

7. The method of claim 6, wherein percutaneously introducing the attachment elements and the connector comprises introducing the attachment elements and the connector from one side of the spinal midline.

8. The method of claim 6, wherein percutaneously introducing the attachment elements and the connector comprises introducing the attachment elements and the connector from a posterior approach.

9. The method of claim 1, wherein the first and second attachment elements comprise hooks for engaging the spinous processes or sacrum.

10. The method of claim 9, wherein engaging the attachment elements to the spinous processes or sacrum comprises introducing the hooks in a retracted configuration and pivoting the hooks relative to the connector to capture the spinous processes or sacrum.

11. The method of claim 10, wherein the first attachment element comprises a superior hook and the second attachment element comprises an inferior hook, and wherein engaging the first attachment element comprises engaging the superior hook to a superior surface of the first spinous process and engaging the second attachment element comprises engaging the inferior hook to an inferior surface of the second spinous process or sacrum.

12. The method of claim 1, wherein providing the reinforcement member comprises providing a reinforcement sleeve disposed over the one connector.

13. The method of claim 1, wherein the one connector comprises a superior segment and an inferior segment, and wherein the one connector further comprises a compliance member attached to the superior and inferior segments of the connector.

14. The method of claim 13, wherein providing the reinforcement member comprises providing a slide assembly adjacent to the compliance member, and wherein the slide assembly aligns the superior and inferior segments of the connector.

* * * * *